(12) United States Patent
Clasen et al.

(10) Patent No.: US 8,361,295 B2
(45) Date of Patent: Jan. 29, 2013

(54) METHOD FOR PRODUCING METALLIC MOULDED BODIES COMPRISING A CERAMIC LAYER, METALLIC MOULDED BODY, AND THE USE OF THE SAME

(75) Inventors: Rolf Clasen, Saarbrücken (DE); Sascha Kühn, Saarbrücken (DE)

(73) Assignee: eZelleron GmbH, Dresden (DE)

( * ) Notice: Subject to any disclaimer, the term of this patent is extended or adjusted under 35 U.S.C. 154(b) by 1010 days.

(21) Appl. No.: 10/543,267

(22) PCT Filed: Jan. 23, 2004

(86) PCT No.: PCT/DE2004/000103
§ 371 (c)(1),
(2), (4) Date: Jun. 14, 2006

(87) PCT Pub. No.: WO2004/067808
PCT Pub. Date: Aug. 12, 2004

(65) Prior Publication Data
US 2006/0231402 A1    Oct. 19, 2006

(30) Foreign Application Priority Data

Jan. 24, 2003 (DE) .................................. 103 02 943
Sep. 16, 2003 (DE) .................................. 103 43 034

(51) Int. Cl.
*C25D 13/02* (2006.01)
(52) U.S. Cl. ........................................... 204/491
(58) Field of Classification Search ............... 204/491
See application file for complete search history.

(56) References Cited

U.S. PATENT DOCUMENTS

| 4,684,386 | A |   | 8/1987 | Clasen |
| 5,002,647 | A |   | 3/1991 | Tanabe et al. |
| 5,120,444 | A |   | 6/1992 | Clasen |
| 5,211,822 | A | * | 5/1993 | Alary et al. .......... 210/500.23 |
| 5,830,340 | A | * | 11/1998 | Iljitch et al. .................. 204/471 |
| 5,998,056 | A |   | 12/1999 | Divisek et al. |
| 6,217,732 | B1 |   | 4/2001 | Schuh et al. |
| 6,410,160 | B1 | * | 6/2002 | Landin et al. ................. 428/613 |
| 6,803,138 | B2 | * | 10/2004 | Seabaugh et al. .............. 429/30 |
| 6,887,361 | B1 | * | 5/2005 | Visco et al. ................... 204/491 |
| 2004/0053767 | A1 |   | 3/2004 | Schwertfeger et al. |

FOREIGN PATENT DOCUMENTS

| DE | 195 20 458 | 12/1996 |
| DE | 195 24 750 | 1/1997 |
| DE | 195 24 750 | 9/1997 |
| DE | 100 44 163 | 4/2002 |
| EP | 0 200 242 | 11/1986 |
| EP | 0 200 242 | 12/1986 |
| EP | 0 439 938 | 8/1991 |
| EP | 0 446 999 | 9/1991 |
| EP | 0 525 844 | 2/1993 |
| EP | 0 829 103 | 12/1999 |
| JP | 2001 31 6874 | 11/2001 |
| JP | 2001-316874 | 11/2001 |

OTHER PUBLICATIONS

Kuehn S. et al., "Impregnation of nickel foils with nanocrystalline ceria as anodes for solid oxide fuel cells SOFC," Ceram. Eng. Sci. Proc. (USA), Ceramic Engineering and Science Proceedings, 2003, American Ceramic Soc., USA, vol. 24, No. 3, Jan. 2003, pp. 305-310. XP001194516 (ISR).

Czerwinski F. et al, "Optimizing properties of Ce0₂ sol-gel coatings for protection of metallic . . . ," Department of Met. Eng., Elsevier Science, S.A., vol. 289, No. 1, Nov. 30, 1996, pp. 213-219. XP004055570 (ISR).

K. Kobayashi et al., "Supported ZR(Sc)O₂ SOFCs for reduced temperature prepared . . . ," Jun. 7, 2002. http://www.sciencedirect.com/science.

K. Kobayashi, I. Takahashi, M. Shiono and M. Dokiya, "Supported ZR(Sc)O₂ SOFCs for reduced temperature prepared by electrophoretic deposition", Dec. 2002. http://www.sciencedirect.com/science.

Kuehn S et al: Impregnation of nickel foils with nanocrystalline ceria as aNodes for solid oxide fuel cells SOFC Ceram. Eng. Sci. Proc. (USA), Ceramic Engineering and Science Proceedings, 2003, American Ceramic Soc, USA, vol. 24, No. 3, Jan. 26, 2003, pp. 305-310, XP001194516 ISSN 0196-6219 abstract (Intl. Srch. Rep.).

Czerwinski F et al: "Optimizing properties of Ce02 sol-gel coatings for protection of metallic substrates against high temperature oxidation" Thin Solid Films, Elsevier-Sequoia S.A Lausanne, Ch, vol. 289, No. 1, Nov. 30, 1996, pp. 213-219, XP004055570 ISSN: 0040-6090 abstract (Intl. Srch. Rep.).

\* cited by examiner

*Primary Examiner* — Kishor Mayekar
(74) *Attorney, Agent, or Firm* — Collard & Roe, P.C.

(57) ABSTRACT

The invention relates to a method for producing metallic moulded bodies comprising a ceramic layer according to the membrane method, whereby a porous metallic membrane is used. The aim of the invention is to provide a cost-effective, rapid method which is as non-polluting as possible for producing metallic moulded bodies comprising a ceramic layer according to the membrane method using a porous metallic membrane, whereby the penetration depth, the green density and the deposition speed of the ceramic particles in the metallic membrane can be controlled. To this end, the porous metallic membrane is sealed by electrophoretic deposition of ceramic particles in the pores of the metallic membrane, the metallic membrane being arranged between two electrodes for the electrophoretic deposition, and the space between an electrode and the metallic membrane being filled with a dispersion containing the ceramic particles to be deposited in the pores and a dispersant.

23 Claims, No Drawings

METHOD FOR PRODUCING METALLIC MOULDED BODIES COMPRISING A CERAMIC LAYER, METALLIC MOULDED BODY, AND THE USE OF THE SAME

CROSS REFERENCE TO RELATED APPLICATIONS

Applicants claim priority under 35 U.S.C. §119 of German Application No. 103 02 943.5 filed on Jan. 24, 2003 and German Application No. and 103 43 034.2 filed on Sep. 16, 2003. Applicants also claim priority under 35 U.S.C. §365 of PCT/DE2004/000103 filed on Jan. 23, 2004. The international application under PCT article 21(2) was not published in English.

BACKGROUND OF THE INVENTION

1. Field of the Invention

The invention relates to a method for producing metallic formed articles with a ceramic layer by the membrane method, wherein a porous metallic membrane is used, a metallic formed article with a ceramic layer, and the use of such a metallic formed article.

2. Description of the Related Art

DE 195 24 750 A1 describes the production of a ceramic layer on the surface of a ceramic formed article, by applying powder particles on a metallic membrane by electrophoretic deposition. A stabilized suspension is used for this purpose.

DE 195 20 458 A1 describes a device for the electrophoretic coating of substrates with two main electrodes to produce a homogeneous electric field and means of arrangement for positioning a substrate within the homogeneous electrical region of the electric field. There are also means of homogenizing the electric field, for example auxiliary electrodes that counteract the distortion of the electric field by the substrate.

U.S. Pat. No. 5,002,647 A discloses a method for producing thick films, in which a powdered starting material is introduced into solvent and an electrical potential is then applied between the electrodes placed in the solution, whereby the powder is deposited on a substrate connected to the cathode. A special solvent system is suggested for this method.

JP 2001316874 A describes a corresponding method in which an electrode is placed in the interior of a nonconducting porous substrate, so that the substrate is coated when a potential is applied.

However, these publications are concerned with conventional electrophoretic deposition, while in the present case, on the other hand, electrophoretic deposition occurs by the membrane method as disclosed by EP 0 446 999 B1.

In this case, in contrast to conventional electrophoretic deposition, a membrane is placed between anode and cathode to separate physically the pH change in the vicinity of the electrodes caused by $H^+$ and $OH^-$ ions from the place of deposition. The evolution of gas that takes place because of the electrolytic dissociation of water can also not affect the particle motion and deposition because of this spatial separation.

Porous metallic formed articles, because of their high stability accompanied by low densities, are used in many industrial sectors. Examples that may be mentioned are filter membranes, structural elements in light construction, implant materials, and anodes for solid oxide fuel cells (SOFCs).

In many cases it is necessary or of great benefit to introduce a second phase (for example, a ceramic phase) that provides catalytic properties, biocompatibility, or other physical characteristics (ion conduction in particular), and/or enables better adhesion to the surrounding material.

A gradual transition between the materials with different thermal expansions is desirable in temperature-stressed material composites (for example, the anode-electrolyte layer in the SOFCs), in order to avoid stresses and cracking. An additional ceramic component is necessary for using metallic formed articles as anodes in solid oxide fuel cells. It makes ion conduction possible in the used volume of the anode and improves the adhesion of the electrolyte layer.

There are two types of anodes that differ in principle: Supporting anodes carry the entire 3-layer system of the SOFC and are between 300 µm and 1,500 µm thick. Nonsupporting anodes such as those described in EP 0 829 103 B1, for example, are thinner, about 50 µm.

Three different configurations of the microstructure are known. Either a mixture of the ceramic and metallic particles is used (for example, EP 0 525 844 B1). However, anodes consisting of a simple mixture of ceramic and metal have numerous drawbacks: First, one is bound to percolation theory and the necessary porosity of 30% can only just be achieved. Furthermore, this configuration tends toward superpotential losses. Also, the metal is not protected against corrosion in this configuration.

It is possible alternatively to configure the microstructure by partially enveloping or coating a ceramic framework with metal, or coating a metallic framework with a ceramic. These two alternatives are preferred over a mixture of ceramic and metallic particles, but are much more costly to produce. An important advantage of the coated metallic framework consists in the fact that the metal is protected against corrosive attack, which for some time has been held responsible as the reason for the degradation and failure of SOFC layers.

The following production methods are known for this:
1. Preparation of supporting anodes by pressing or hot-pressing. Microstructure: mixture.
2. Preparation of supporting anodes by thermal spray methods, particularly plasma spraying. Microstructure: mixture.
3. Application of the anodes as nickel slips on the electrolyte layer. A very tedious and cost-intensive impregnation of the anode with YSZ follows, by electrochemical gas phase deposition, EVD, at high temperatures. The anodes made in this way achieve the highest efficiency in the present state of the art. Microstructure: metal framework with ceramic coating.
4. Anode preparation by film printing. Microstructure: mixture.
5. Construction of anodes as a mixture of two phases.
6. Impregnation of sintered nickel membranes with stabilized YSZ suspension by saturation, as shown in EP 0 439 938 B1.

The high costs and the considerable time required, the toxic gases formed, and poor controllability are drawbacks in the 3rd method. A graduated coating cannot be produced by this method.

The 6th method requires two sintering steps. Only low green densities can be achieved by saturation.

SUMMARY OF THE INVENTION

All of the known methods have the drawback that they cannot produce a graduated density curve in the formed articles.

The purpose of the invention is thus to provide an economical, fast method as free as possible of harmful substances for producing metallic formed articles by the membrane method with a ceramic coating starting from a porous metallic membrane. The depth of penetration, the green density, and the rate of deposition of the ceramic particles in the metal membrane should also be controllable.

This objective is reached pursuant to the invention by providing that the porous metallic membrane is post-densified by electrophoretic deposition of ceramic particles in the pores of the metallic membrane, and that the metallic membrane is placed between two electrodes for the electrophoretic deposition by the membrane method (EP 200 242 A1), for which a metallic membrane can be used in this case, especially a metallic membrane combined with a second or multiple metallic or nonmetallic membrane(s). The space between one electrode and the face of the metallic membrane to be impregnated is filled with a dispersion that contains the ceramic particles to be deposited in the pores and a dispersant. Additives (especially dispersing aids) can also be added. The membrane is at a potential that corresponds to >0 to 90% (based on the electrode in the compensation chamber) of the voltage applied to the electrodes.

EP 200 242 has a U.S. equivalent which is U.S. Pat. No. 4,684,386, which discloses that the porous membrane 1 of silica glass is not connected to the cathode 3 or the anode 4. The disclosure of U.S. Pat. No. 4,684,386, is herewith incorporated by reference. Thus the porous metallic membrane of the present invention is not an electrode.

The method pursuant to the invention leads to a densification of the formed article by deposition of the ceramic particles in the pores of the metallic membrane. The impregnated and post-densified depth and the increase of green density vary, depending on the process parameters, for example such as the electric field, the degree of filling of the dispersion, particle diameter, zeta potential, etc., and on the properties of the membrane, the pore radius distribution, and the green density. Surprisingly, the deposition of ceramic particles by the method pursuant to the invention also succeeded within a boundary layer in the pores of the metallic membrane. A metal-ceramic material composite can be successfully produced in this way quickly, cleanly, and economically.

The formation of the ceramic layer is controllable by applying an electric field. The ceramic particles are accelerated by the electric field and can penetrate more deeply into the pores of the boundary layer. It is thus possible to provide a formed article of the type described above with a selectively set gradient of ceramic impregnation.

A refinement of the invention consists in saturating the metallic membrane with a compensation solution prior to its insertion between the electrodes. The dispersion is different from the compensation solution.

It is provided in the context of the invention for the dispersant to be a polar or nonpolar organic solvent.

It is advantageous for the solvent to be selected from the group consisting of alcohols, esters, ethers, organic acids, saturated or unsaturated hydrocarbons, and water, or a mixture thereof, and preferably to be selected from the group consisting of methanol, ethanol, propanol, acetone, and water, or a mixture thereof.

Acetone and water and their mixtures are preferred as solvent, and water is very highly preferred.

It is provided pursuant to the invention that the viscosity of the dispersion is between 1 and 1,000 mPa.s, preferably between 1 and 100 mpa.s.

It can also be beneficial to use different dispersions in succession.

This can be done in particular to apply a ceramic layer on an anode subsequently.

The method pursuant to the invention results in good anchoring of the ceramic layer, which can be further improved by the existence of a bimodal particle size distribution (in which another powder is present with larger particles, around which the smaller particles are arranged). Besides resulting in better film adhesion, the degree of filling and additives in the suspension, the particle size distribution in the suspension (especially by introducing sinter-active powders such as nano-$CeO_2$, nano-GDC), and the deposition parameters of the electrophoresis result in an adaptable green density of the additionally applied ceramic layer and therefore to adaptable shrinkage upon sintering. For this reason, in contrast to DE 195 24 750 A1, application and sintering in one step becomes possible.

It is expedient for a d.c. voltage of 5 V to 100 V or an electric field strength of 0.1 V/cm to 20 V/cm to be applied for the electrophoretic deposition.

A deposition time between one second and 30 minutes is also provided.

It is also part of the invention for the metallic green article to be subjected to sintering.

Almost no sagging of the specimen occurs during sintering in the method pursuant to the invention, so that the risk of cracking is distinctly reduced. It can be advantageous not to carry out the sintering completely, in order to obtain a definite residual porosity of the ceramic layer.

It is suitable here for the sintering temperature to be between 900° C. and 1,700° C., preferably between 1,000° C. and 1,400° C.

A preferred embodiment of the invention consists in the metallic formed article consisting of nickel.

Such formed articles, for example, can be produced by compressing nickel powder.

Cerium oxide particles ($CeO_2$), especially gadolinium-doped cerium particles (GDC), or zirconium oxide particles, especially yttrium-stabilized zirconium oxide (YSZ), are preferably used as ceramic particles.

It has proved to be particularly advantageous for the ceramic particles to be in bimodal size distribution. This means that two powders with different average particle diameters are used.

A metallic formed article with a ceramic layer, characterized by the fact that it has been produced by one of the methods pursuant to the invention, is also within the scope of the invention.

The additional ceramic layer can also be applied in one step with the impregnation if the suspension has a bimodal particle size distribution and contains a large proportion of very fine particles.

The metallic formed article can be a nickel article with a cerium oxide coating, preferably with a bimodal cerium oxide coating. In particular, it can be a nickel-GDC composite membrane.

The use of such a metallic formed article, especially with an additional ceramic layer, as an anode for solid oxide fuel cells (SOFCs) is also within the scope of the invention.

According to the invention, such a metallic formed article with an additionally applied ceramic layer can also be used as an anode-electrolyte layer composite for solid oxide fuel cells (SOFCs).

In summary, the advantages of the invention consist in the fact that an economical, fast method free of harmful substances for producing metallic formed articles with a ceramic layer has been provided within the scope of the invention, with the depth of penetration, the green density, and the rate of deposition of the ceramic particles in the metal membrane being controllable by the process parameters.

DETAILED DESCRIPTION OF PREFERRED EMBODIMENTS

The invention will be discussed in further detail below with reference to examples of embodiment.

EXAMPLES OF EMBODIMENT

Example 1

A dispersion of gadolinium-doped cerium oxide powder (GDC) that has an average particle diameter of 300 nm and water with a solids content of 60 wt. % is prepared and stabilized with 0.2 wt. % TMAH. A compensation solution is prepared with twice-distilled water with the addition of 0.2 wt. % TMAH. A nickel membrane is prepared by uniaxial compression of nickel powder that has an average particle diameter of 45 μm.

The nickel membrane, which has previously been saturated with the compensation solution, is clamped in between the electrodes, so that the space between the two electrodes of the electrophoresis cell is divided into two chambers in the ratio of 2:3.

The dispersion is loaded into the larger chamber of the electrophoresis cell. The other chamber is filled with the compensation solution. The total distance between the two electrodes is 6 cm. A d.c. voltage of 20 V is then applied to the electrodes of the electrophoresis chamber for a period of two minutes.

The nickel-GDC composite membrane after drying has a gradual density change of 20 vol. % on the impregnated surface down to a depth of about 200 μm. A cohesive layer of GDC with vermicular structure can be seen in SEM photographs after sintering at 1,250° C.

Example 2

A dispersion of GDC powders with bimodal particle size distribution, with the coarser powder having an average particle diameter of 1,000 nm and with the fine powder having an average particle diameter of 15 nm, is prepared in water and is stabilized with 0.2 wt. % TMAH. For this purpose, 20 wt. % of the fine powder and 20 wt. % of the coarse powder are dispersed in water. A compensation solution is prepared with twice-distilled water and 0.2 wt. % HCl is added. A nickel membrane is prepared by uniaxial compression of nickel powder that has an average particle diameter of 45 μm.

The nickel membrane, which has previously been saturated with the compensation solution, is clamped in between the electrodes, so that the space between the two electrodes of the electrophoresis cell is divided into two chambers with a ratio of 2:3.

The dispersion is loaded into the larger chamber of the electrophoresis cell. The other chamber is filled with the compensation solution. The total distance between the two electrodes is 6 cm. A d.c. voltage of 15 V is then applied to the electrodes of the electrophoresis chamber for a period of three minutes.

In addition to impregnation, a layer 150 μm can also be applied. The specimen is dried in a desiccator at room temperature for 24 h. Because of the high green density, the layer can dry without cracking. The substrate is not stressed during the sintering at 1,350° C. and a dense layer on the substrate is obtained that is anchored very well by the GDC gradient beneath it and adheres well.

The invention claimed is:

1. Method for producing metallic formed articles with a ceramic layer by a membrane method, using a porous metallic membrane, wherein the porous metallic membrane is post-densified by electrophoretic deposition of ceramic particles in the pores of the metallic membrane, and wherein the metallic membrane is placed between two electrodes for the electrophoretic deposition at a space between one electrode and a face of the metallic membrane, and the space between one electrode and the face of the metallic membrane is filled with a dispersion that contains the ceramic particles to be deposited in the pores and a dispersant; and wherein there is a gradual change in density after drying of the metallic membrane; and wherein the porous metallic membrane is not an electrode.

2. Method pursuant to claim 1, wherein the metallic membrane is saturated with a compensation solution prior to being introduced between the electrodes.

3. Method pursuant to claim 1, wherein the dispersant is a polar organic solvent or nonpolar organic solvent, or water.

4. Method pursuant to claim 1, wherein the dispersant is a solvent selected from the group consisting of alcohols, esters, ethers, organic acids, saturated or unsaturated hydrocarbons, and water, or a mixture thereof.

5. Method pursuant to claim 1, wherein the viscosity of the dispersion is between 1 and 1,000 mPa.s.

6. Method pursuant to claim 1, wherein the different dispersions are used in succession.

7. Method pursuant to claim 1, wherein an electric d.c. voltage of 5 V to 100 V or an electric field strength of 0.1 V/cm to 20 V/cm is applied for the electrophoretic deposition.

8. Method pursuant to claim 1, wherein the time of deposition is between one second and 30 minutes.

9. Method pursuant to claim 1, wherein further comprising sintering the porous metallic membrane following post-densification.

10. Method pursuant to claim 9, wherein the sintering temperature is between 900°C. and 1,700°C.

11. Method pursuant to claim 1, wherein the metallic membrane is made from nickel.

12. Method pursuant to claim 1, wherein the ceramic particles are cerium oxide particles ($CeO_2$).

13. Method pursuant to claim 12, wherein the ceramic particles are gadolinium-doped cerium oxide particles (GDC).

14. Method pursuant to claim 1, wherein the ceramic particles are present in bimodal size distribution.

15. Method pursuant to claim 14, wherein the bimodal particle size distribution comprises two powders with different average particle diameters being used.

16. Method pursuant to claim 15, wherein the bimodal particle size distribution contains a large proportion of very fine particles.

17. Method pursuant to claim 1, wherein the gradual change in density is on the impregnated surface down to a depth of about 200 μm.

18. Method for producing metallic formed articles with a ceramic layer by a membrane method, using a porous metallic membrane, wherein the porous metallic membrane is post-densified by electrophoretic deposition of ceramic particles in the pores of the metallic membrane;

wherein the metallic membrane is placed between two electrodes for the electrophoretic deposition at a first space between one electrode and a first face of the metallic membrane, and the first space between said one electrode and said first face of the metallic membrane is filled with a dispersion that contains the ceramic particles to be deposited in the pores and a dispersant; and a second space between a second electrode and a second face of the metallic membrane is filled with a compensation solution; and wherein there is a gradual change in density after drying of the metallic membrane; and wherein said dispersion is different from said compensation solution.

19. Method pursuant to claim 18, wherein the metallic membrane is saturated with said compensation solution prior to being introduced between the electrodes.

20. Method pursuant to claim 18, wherein the bimodal particle size distribution comprises two powders with different average particle diameters being used.

21. Method pursuant to claim 18, wherein the bimodal particle size distribution contains a large proportion of very fine particles.

22. Method pursuant to claim 18, wherein the gradual change in density is on the impregnated surface down to a depth of about 200 μm.

23. Method pursuant to claim 18, wherein said porous metallic membrane is not an electrode.

* * * * *

UNITED STATES PATENT AND TRADEMARK OFFICE
CERTIFICATE OF CORRECTION

PATENT NO. : 8,361,295 B2 Page 1 of 1
APPLICATION NO. : 10/543267
DATED : January 29, 2013
INVENTOR(S) : Clasen et al.

It is certified that error appears in the above-identified patent and that said Letters Patent is hereby corrected as shown below:

On the Title Page:

The first or sole Notice should read --

Subject to any disclaimer, the term of this patent is extended or adjusted under 35 U.S.C. 154(b) by 1451 days.

Signed and Sealed this
First Day of September, 2015

Michelle K. Lee
*Director of the United States Patent and Trademark Office*